(12) United States Patent
Cojbasic

(10) Patent No.: US 7,549,968 B2
(45) Date of Patent: Jun. 23, 2009

(54) DYNAMIC, ADJUSTABLE ORTHOPEDIC DEVICE

(76) Inventor: Milun Cojbasic, Milana Jonvanovica St. 57/1, 3200 Cacak (YU)

( * ) Notice: Subject to any disclaimer, the term of this patent is extended or adjusted under 35 U.S.C. 154(b) by 336 days.

(21) Appl. No.: 11/323,534

(22) Filed: Dec. 29, 2005

(65) Prior Publication Data

US 2007/0156074 A1    Jul. 5, 2007

(51) Int. Cl.
    *A61F 5/00* (2006.01)
(52) U.S. Cl. .............................. 602/5; 602/19; 128/874
(58) Field of Classification Search ............. 602/5, 602/16, 19; 128/845, 846, 869, 876
    See application file for complete search history.

(56) References Cited

U.S. PATENT DOCUMENTS

| | | | |
|---|---|---|---|
| 4,518 A | 5/1846 | Sullivan | |
| 9,826 A | 7/1853 | Abbe | |
| 709,055 A | 11/1902 | Sheldon | |
| 954,005 A | 4/1910 | Roth | |
| 1,043,648 A | 11/1912 | Weaver | |
| 1,722,205 A | 7/1929 | Freund | |
| 1,803,556 A | 5/1931 | Nugent | |
| 2,060,173 A | 11/1936 | Buschenfeldt | |
| 2,492,383 A | 12/1949 | Jones | |
| 2,820,455 A | 1/1958 | Hall | |
| 2,828,737 A | 4/1958 | Hale | |
| 2,886,031 A * | 5/1959 | Robbins | 602/19 |
| 3,177,869 A | 4/1965 | Bartels | |
| 3,364,926 A | 1/1968 | Alderson | |
| 3,548,817 A * | 12/1970 | Mittasch | 602/36 |
| 3,596,655 A | 8/1971 | Corcoran | |
| 3,601,123 A | 8/1971 | McFarland | |
| 3,675,646 A | 7/1972 | Corcoran | |
| 3,771,513 A | 11/1973 | Velazquez | |
| 3,776,224 A | 12/1973 | McFarland | |
| 3,945,376 A | 3/1976 | Kuehnegger | |
| 3,957,040 A | 5/1976 | Calabrese | |
| 4,383,523 A | 5/1983 | Schurman | |
| 4,539,979 A | 9/1985 | Bremer | |
| 4,620,530 A | 11/1986 | Lanier et al. | |
| 4,715,362 A | 12/1987 | Scott | |
| 4,721,102 A * | 1/1988 | Pethybridge | 602/19 |
| 4,732,144 A | 3/1988 | Cunanan | |
| 4,735,196 A | 4/1988 | Krag et al. | |
| 4,807,605 A | 2/1989 | Mattingly | |
| 4,827,915 A | 5/1989 | Gorsen | |
| 4,951,655 A | 8/1990 | MacMillan et al. | |
| 5,046,490 A | 9/1991 | Young et al. | |
| 5,088,482 A | 2/1992 | McGuinness | |
| 5,171,296 A | 12/1992 | Herman | |
| 5,195,947 A | 3/1993 | Bode | |
| 5,242,377 A | 9/1993 | Boughner et al. | |
| 5,259,833 A | 11/1993 | Barnett | |
| 5,405,313 A * | 4/1995 | Albin | 602/19 |
| 5,782,783 A | 7/1998 | Young et al. | |
| 5,876,361 A * | 3/1999 | Harris | 602/19 |
| 6,267,741 B1 | 7/2001 | Lerman | |
| 6,280,405 B1 * | 8/2001 | Broselid | 602/36 |
| 6,315,746 B1 | 11/2001 | Garth et al. | |

(Continued)

*Primary Examiner*—Michael A. Brown
(74) *Attorney, Agent, or Firm*—Amster, Rothstein & Ebenstein LLP

(57) ABSTRACT

Provided are dynamic, adjustable orthopedic devices for providing support to the spine of a vertebrate. Also provided are methods of supporting the spinal column of a vertebrate using the device.

21 Claims, 4 Drawing Sheets

U.S. PATENT DOCUMENTS 6,681,770 B1  1/2004  Dreher
6,770,047 B2  8/2004  Bonutti
2003/0220594 A1  11/2003  Halvorson et al.
2004/0204666 A1  10/2004  Marsh

* cited by examiner

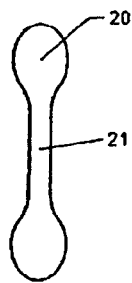
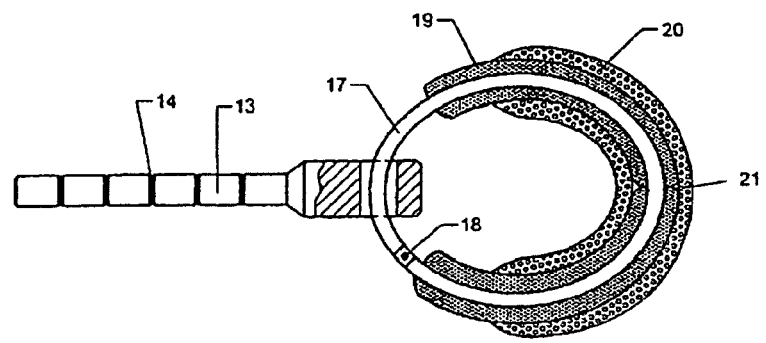
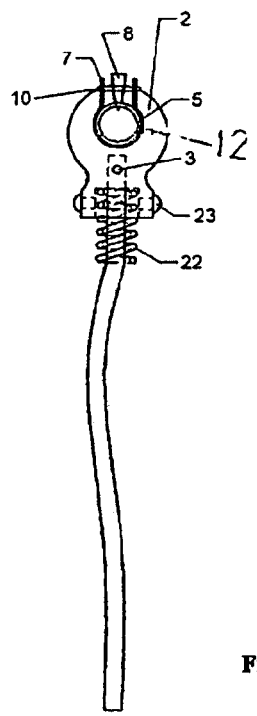
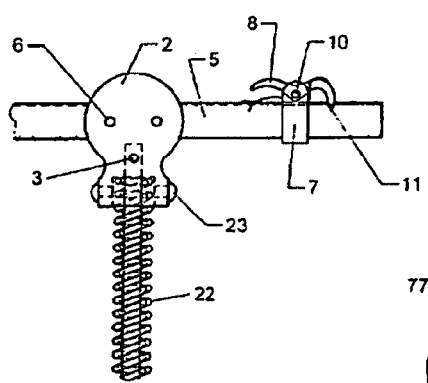
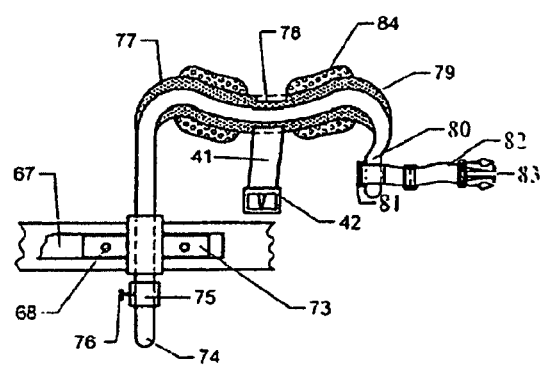
Figure 6
Figure 5
Figure 3
Figure 4
Figure 7

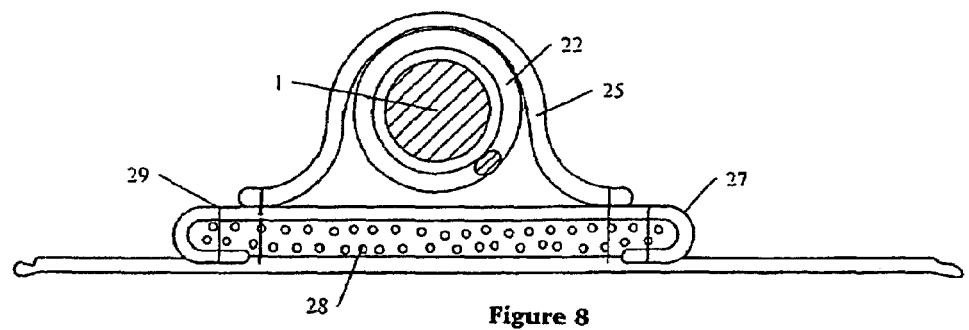
Figure 8
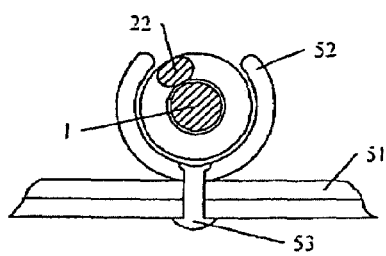
Figure 10
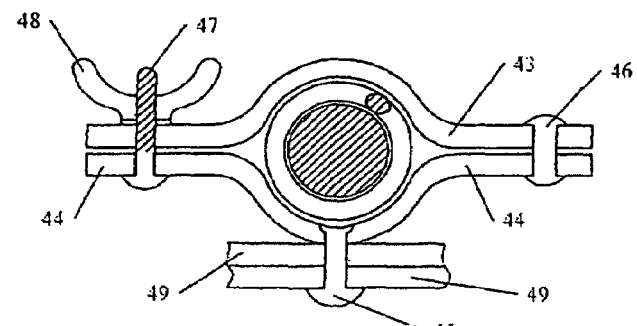
Figure 9
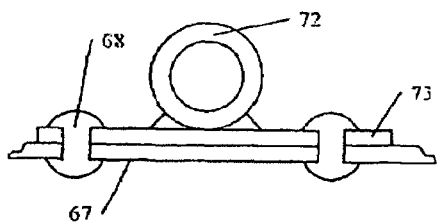
Figure 12
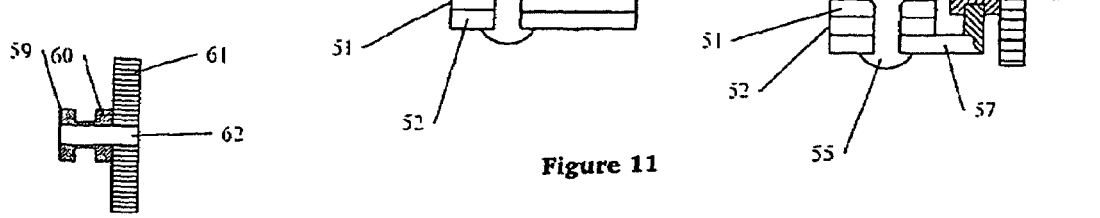
Figure 11
Figure 13

DYNAMIC, ADJUSTABLE ORTHOPEDIC DEVICE

CROSS-REFERENCE TO RELATED APPLICATION

This application claims the benefit of Serbia and Montenegro Application No. P/1163/04, filed Dec. 30, 2004.

BACKGROUND OF THE INVENTION

1. Field of the Invention

The present invention generally relates to devices and methods providing spinal support. More specifically, the invention provides a device in the form of an interconnected belt and vest that can be adjusted to provide various levels of spinal support.

2. Description of the Related Art

Various devices are known that provide support for the spinal column and/or neck. See U.S. Pat. Nos. 4,518; 9,826; 709,055; 954,005; 1,043,648; 1,722,205; 1,803,556; 2,060,173; 2,492,383; 2,820,455; 2,828,737; 3,177,869; 3,364,926; 3,596,655; 3,601,123; 3,675,646; 3,771,513; 3,776,224; 3,945,376; 3,957,040; 4,383,523; 4,539,979; 4,620,530; 4,715,362; 4,732,144; 4,735,196; 4,807,605; 4,827,915; 4,951,655; 5,046,490; 5,088,482; 5,171,296; 5,195,947; 5,242,377; 5,259,833; 5,624,387; 5,782,783; 6,267,741; 6,315,746; 6,681,770; and 6,770,047; U.S. Patent Publications 2003/0220594; and 2004/0204666; and Serbia and Montenegro Patent Application No. P/1163/04. However, all of those devices are deficient in providing a static burdening of joints and muscles of the spinal columns, while preserving its dynamic functions and providing active and dynamic treatment of deformities or certain pathologic conditions, and providing prevention and rehabilitation of deformities and immobilization of various injuries, in an adjustable device providing various levels of support and immobilization for patients of various sizes.

It is therefore an object of the present invention to provide improved devices and methods for providing adjustable spinal support for treatment, correction immobilization and/or anti-static relaxation of the spinal column.

It is a further object of the invention to provide this support with a light and comfortable device that can be worn under or over clothing.

It is an additional object of the invention to provide several adjustable areas of the device to allow use during various stages of treatment and for patients of various sizes and requiring various degrees of spinal immobilization.

SUMMARY OF THE INVENTION

It has been found that the above and related objects of the present invention are obtained by the use of the adjustable orthopedic device described herein.

Accordingly, the present invention is directed to an orthopedic device for providing support to the spine of a vertebrate. The device comprises:

(a) a waist belt;

(b) a vest having portions that are capable of surrounding the torso of the vertebrate above the waist belt, wherein the portions of the vest that surround the torso can attach to each other; and (c) a support column comprising:

(i) an elongated rod attached to the vest and extending substantially the length of the vest adjacent and parallel to the spine of the vertebrate;

(ii) an elongated spring surrounding the rod and extending substantially the length of the rod, the spring fixed in relation to the rod at the top and bottom of the spring; and (iii) a mechanism having a top, a bottom and an adjusting device, the top of the mechanism attached to the vest near a central portion of the rod and the bottom of the mechanism attached to the waist belt, wherein actuating the adjusting device lengthens or shortens the distance from the top to the bottom of the mechanism.

The invention is also directed to an orthopedic device for providing support to the spine of a human. The device comprises:

(a) a waist belt;

(b) a vest having portions that are capable of surrounding the torso of the vertebrate above the waist belt, wherein the portions of the vest that surround the torso can attach to each other, wherein the portions of the vest that surround the torso can attach to each other using Velcro®;

(c) a support column comprising:

(i) an elongated rod attached to the vest and extending substantially the length of the vest adjacent and parallel to the spine of the vertebrate;

(ii) an elongated spring surrounding the rod and extending substantially the length of the rod, the spring fixed in relation to the rod at the top and bottom of the spring, wherein the bottom of the spring is fixed to the rod using a mechanism that can raise or lower the bottom of the spring in relation to the rod; and (iii) a mechanism having a top, a bottom and an adjusting device, the top of the mechanism attached to the vest near a central portion of the rod and the bottom of the mechanism attached to the waist belt, wherein actuating the adjusting device lengthens or shortens the distance from the top to the bottom of the mechanism, wherein the mechanism comprises a series of diagonally crossing segments attached at their ends and wherein the adjusting device comprises an adjustment screw and nut for adjusting the degree of separation between the opposing ends of said crossing segments;

(d) a horizontal elongated crosspiece attached at its center to the top of the vest near the top of the elongated rod, wherein the ends of the crosspiece having loops capable of surrounding the arms of the vertebrate at the shoulders, and wherein the length of the crosspiece is adjustable;

(e) two pairs of straps capable of connecting the vest to the waist belt, wherein one pair of straps is elastic and the other pair of straps is not elastic; and a pair of curved appendages, each fixed at one end to the waist belt, the appendages further having extensions at the other end, wherein the extensions can connect to each other in front of the vertebrate above the waist belt, and wherein the appendages are capable of attaching to the ends of the straps to connect the straps to the waist belt.

Additionally, the invention is directed to methods of supporting the spinal column of a vertebrate. The methods comprise putting the above device on the vertebrate such that the device supports the spinal column of the vertebrate.

BRIEF DESCRIPTION OF THE DRAWINGS

These and other objects, features and advantages of the present invention will be more fully understood by reference to the following detailed description of the presently preferred, albeit illustrative, embodiments of the present invention wherein:

FIG. 3 is a view of one embodiment of the rod and crosspiece, and a bracket connecting the two, of the present invention device.

FIG. 4 is a view of an alternative embodiment of the rod.

FIG. 5 is a view of an embodiment of an end of the crosspiece of the invention, showing a padded shoulder ring.

FIG. 6 is a view of a section of the shoulder cushioning of the padded shoulder ring shown in FIG. 5.

FIG. 7 is a view of one embodiment of the curved appendage of the invention.

FIG. 8 is a cross-section of some embodiments of the invention device through the rod, toward its upper end.

FIG. 9 is a cross-section of some embodiments of the invention device through the rod and the bracket 43.

FIG. 10 is a cross-section of some embodiments of the invention device through the rod and the bracket 52.

FIG. 11 is a cross-section of some embodiments of the invention device through the rod and the adjusting device.

FIG. 12 is a cross-section of some embodiments of the invention device through the curved appendage and the portion of the belt adjacent thereto.

FIG. 13 is a cross-section of an embodiment of a portion of the adjusting device.

DETAILED DESCRIPTION OF THE INVENTION

The present invention provides an orthopedic device for providing support to the spine of a mammal. The device has an adjustable belt that surrounds the waist of the mammal, and an adjustable vest that surrounds the torso of the mammal. Attached to the vest is a rod placed through an elongated spring that runs substantially the length of the mammal's spine, and an adjustment mechanism that adjusts the strength of the support to the spine that is provided by the device.

Thus, the invention is directed to orthopedic devices for providing support to the spine of a vertebrate. The devices comprise (a) a waist belt;

(b) a vest having portions that are capable of surrounding the torso of the vertebrate above the waist belt, wherein the portions of the vest that surround the torso can attach to each other; and (c) a support column. The support column comprises (i) an elongated rod attached to the vest and extending substantially the length of the vest adjacent and parallel to the spine of the vertebrate;

(ii) an elongated spring surrounding the rod and extending substantially the length of the rod, the spring fixed in relation to the rod at the top and bottom of the spring; and (iii) a mechanism having a top, a bottom and an adjusting device, the top of the mechanism attached to the vest near a central portion of the rod and the bottom of the mechanism attached to the waist belt, wherein actuating the adjusting device lengthens or shortens the distance from the top to the bottom of the mechanism. A preferred embodiment of the invention device is illustrated in FIGS. 1-11.

The waist belt can be made of any material and be of any design known in the art such that it can support the mechanism (also referred to herein as a "fine adjustment mechanism") and be securely cinched to the waist of the vertebrate. Preferably, the waist belt can hold a rivet such as is used in the illustrated preferred example, where the waist belt 69 holds rivets that support the mechanism.

The vest preferably includes the backing 29 as well as wings 30, preferably made of cotton, or another appropriate cloth. The ends of the wings preferably include integral belts 31, on which a burdock tape or Velcro® 32 is sewed.

Figure 1:
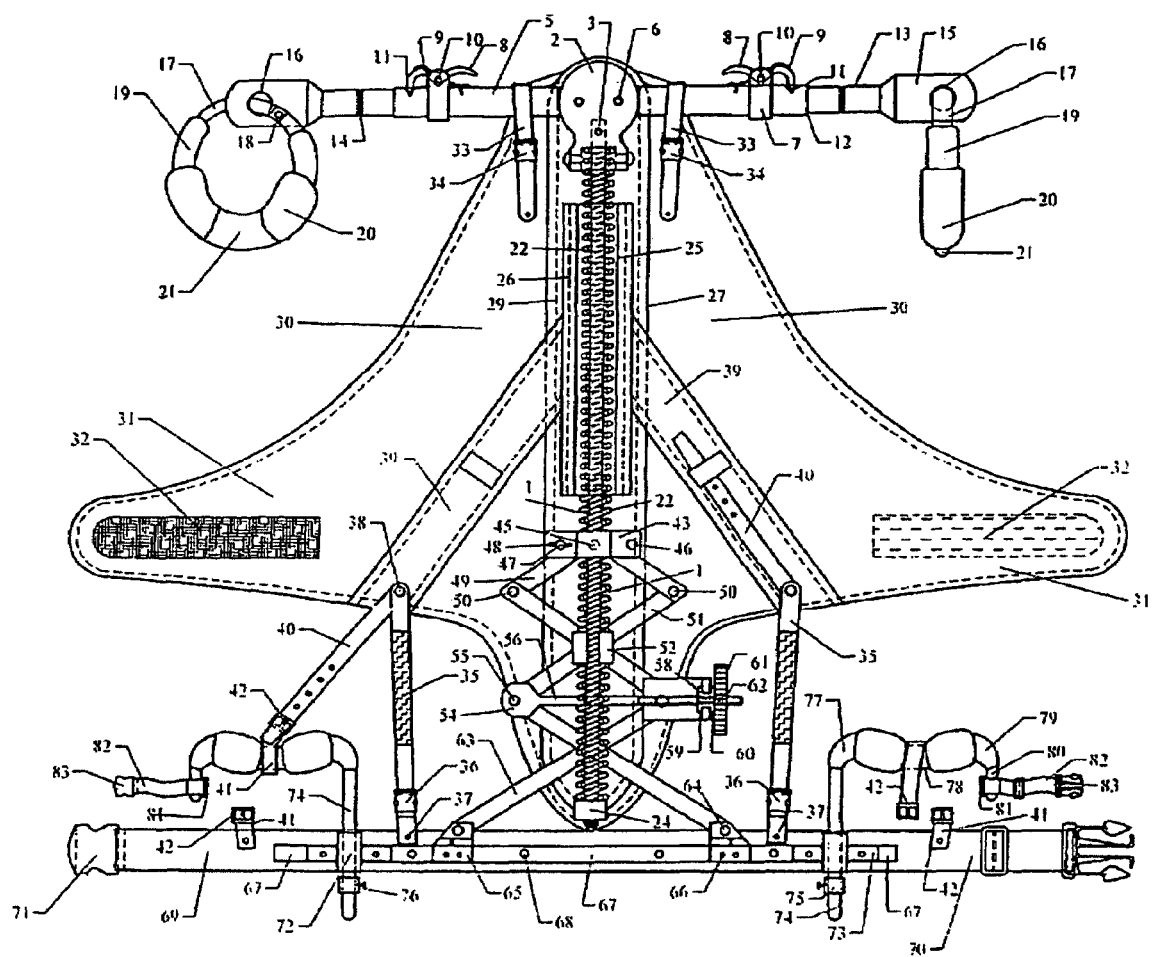
FIG. 1 is a rear elevation of one embodiment of the invention device.

In a preferred embodiment, the elongated rod 1 is of an appropriate metal, e.g., stainless steel or titanium, and is connected at its top to a central connector 2 via a rivet 3. The rod 1 can be curved as appropriate for comfort (FIG. 4). The rod 1 is surrounded by a cylindrical spring 22 extending the length of the rod 1. It is preferably connected to cylindrical opening 23 in central connector 2. The spring 22 is preferably secured at the base of the rod 1. More preferably, the bottom of the spring 22 is fixed to the rod 1 using a coarse adjustment mechanism that can raise or lower the bottom of the spring in relation to the rod 1. Most preferably, this coarse adjustment mechanism utilizes adjustable nut 24. As shown in FIGS. 1 and 8, the spring 22 is preferably partially covered by fabric 25 and is cushioned from the wearer's body by a combination of a cloth 27 and a sponge 28 affixed to a backing 29.

In preferred embodiments, the spring 22 is secured by a cylindrically formed bracket having two parts 43 and 44, which are connected by a rivet 46 at one end. Preferably, at the other end of the bracket, bolt 47 and butterfly nut 48 provides a means to adjust the bracket.

Preferably, the fine adjustment mechanism comprises a series of diagonally crossing segments attached at their ends and wherein the adjusting device comprises an adjustment screw and nut for adjusting the degree of separation between the opposing ends of said crossing segments.

Figure 2:
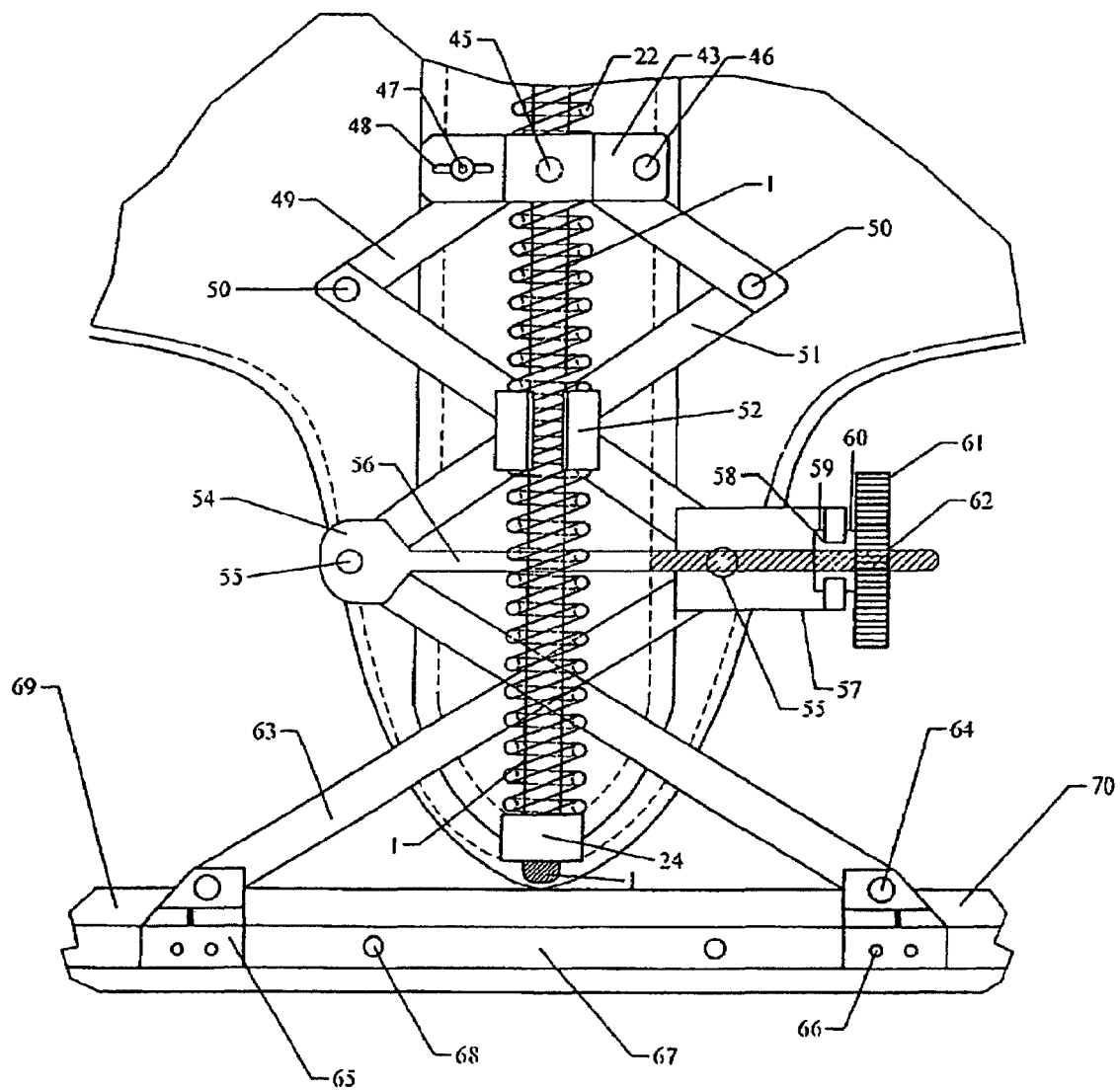
FIG. 2 is a fragmentary view of one embodiment of the adjustable mechanism for adjusting spinal support of the invention device.

A preferred example of a fine adjustment mechanism of the invention is illustrated in FIGS. 1 and 2. Middle segments 51 and lower segments 63 are connected to an adjustment rod 54 via bolts 55. The adjustment rod 54 is threaded at one end and passes through a housing 57 and an adjustment nut 62. Specifically, the adjustment rod 54 passes through a flange 58 formed around an opening 59 in the housing 57. By turning the adjustment nut 62, the fine adjustment mechanism can be elongated or contracted and the load supported by the orthopedic device of the present invention can be adjusted with a high degree of specificity. That is, rotation of the adjustment nut 62 translates to a corresponding adjustment in distance between the points of connection between the middle segments 51 and the lower segments 63, which in turn translates to a corresponding and fine adjustment in the distance between the top and bottom of the fine adjustment mechanism. Lower segments 63 are affixed to a bearing strip 67 via bolts 64. The bearing strip 67 is affixed to the waist belt 69 with rivets 68.

A benefit of the present invention is the improved adjustability provided by the two parts 43 and 44 of the opening are connected to top segments 49 which are in turn connected to middle segments 51 which are in turn connected to lower segments 63. A cylindrical clasp 52 is connected at the point at which the middle segments 51 cross and surround the spring 22 and rod 1. The middle segments 51 and lower segments 63 both intersect between the spring 22 and backing 29.

Preferably, the device further comprises a horizontal elongated crosspiece attached at its center to the top of the vest near the top of the elongated rod, where the ends of the crosspiece capable attaching to the shoulders of the vertebrate. The ends of the crosspiece preferably have loops capable of surrounding the arms of the vertebrate at the shoulders. The length of the crosspiece is adjustable.

A preferred embodiment of the crosspiece 5 is illustrated on FIGS. 1, 3, 5. The upper portions of the vest 30 are attached to crosspiece 5 by belts 33 and buckles 34 looping over the crosspiece 5. The crosspiece 5 is passed through the central connector 2 and held in place with rivets 6. The crosspiece 5 includes an outer support piece 12 and two endpieces 13 (one of each side of the central connector 2), both of which telescope within the outer support piece 12. The outer support piece 12 includes two openings 11 (one on each side of the central connector 2). The two endpieces 13 each have multiple spaced grooves 14 that may be exposed through the openings 11 as the endpieces 13 are telescoped relative to the outer support piece 12. As shown in FIG. 3, the crosspiece 5 has an adjusting spring loaded "rocker arm" having arms 8 and 9, and a pivot point 10. The rocker arms are attached to the crosspiece 5 via a connector 7. The arms 9 may be pivoted into the slitted openings 11 and one of the grooves 14 to lock the endpieces 13 in position relative to the crosspiece 5. The other end of the endpiece 13 has an opening 15, holding a loop 17. The loop 17, preferably includes a bipartite rubber hose 19 and a bottom sponge portion 20 having a flattened center 21. The loop 17 ideally placed to encircle the wearer's shoulders at the armpit joints and positioned so as to cushion the armpit nerves.

In preferred embodiments, the device further comprises at least one pair of straps capable of connecting the vest to the waist belt. The straps are used to tether the vest to the waist belt. The straps can be elastic or not, to provide a desired amount of lateral bending at the waist as desired. Preferably, the device comprises two pairs of straps, where one pair of straps is elastic and the other pair of straps is not elastic.

In a preferred embodiment illustrated in FIG. 1, elastic belts 35 and non-elastic belt 40, are affixed at one end to a connector 38 on the vest. The non-elastic belts 40 can be tied via buckles 41 and 42 in order to provide immobilization capabilities. The elastic belt or belts are tied a waist belt 69, at a rearward point 37 on waist belt 69 via a buckle 36.

The invention device having the above-described straps preferably further comprise a pair of curved appendages, each fixed at one end to the waist belt, the appendages further having extensions at the other end, wherein the extensions can connect to each other in front of the vertebrate above the waist belt, and wherein the appendages are capable of attaching to the ends of the straps to connect the straps to the waist belt.

As shown in FIG. 7, the curved appendages 74 are bent to better fit the body of the wearer and preferably include cushioning in the form of a rubber sleeve 77 and sponge 84. Belts 41 and 42 are used to attach the curved appendages 74 to the waist belt 69 and another set of belts 82 and buckles 83 are used to attach the curved appendages 74 to each other. The curved appendages 74 are connected to the bearing strip 67 via an opening 72 and are limited in their range of vertical motion by an adjustable sleeve 75 and an adjusting screw 76.

In preferred embodiments, the device is capable of being adjusted on the vertebrate to permit some spinal movement. The various ways that the device can be adjusted allows adjustment to independently permit or restrict spinal movement in various directions.

Preferably, the device can provide support to the spine of a mammal, most preferably a human.

The present invention is also directed to the preferred embodiment of the above device for providing support to the spine of a human that is illustrated in FIGS. 1-11. The device comprises:

(a) a waist belt;

(b) a vest having portions that are capable of surrounding the torso of the vertebrate above the waist belt, wherein the portions of the vest that surround the torso can attach to each other, wherein the portions of the vest that surround the torso can attach to each other using Velcro®;

(c) a support column comprising:

(i) an elongated rod attached to the vest and extending substantially the length of the vest adjacent and parallel to the spine of the vertebrate;

(ii) an elongated spring surrounding the rod and extending substantially the length of the rod, the spring fixed in relation to the rod at the top and bottom of the spring, wherein the bottom of the spring is fixed to the rod using a mechanism that can raise or lower the bottom of the spring in relation to the rod; and (iii) a mechanism having a top, a bottom and an adjusting device, the top of the mechanism attached to the vest near a central portion of the rod and the bottom of the mechanism attached to the waist belt, wherein actuating the adjusting device lengthens or shortens the distance from the top to the bottom of the mechanism, wherein the mechanism comprises a series of diagonally crossing segments attached at their ends and wherein the adjusting device comprises an adjustment screw and nut for adjusting the degree of separation between the opposing ends of said crossing segments;

(d) a horizontal elongated crosspiece attached at its center to the top of the vest near the top of the elongated rod, wherein the ends of the crosspiece having loops capable of surrounding the arms of the vertebrate at the shoulders, and wherein the length of the crosspiece is adjustable;

(e) two pairs of straps capable of connecting the vest to the waist belt, wherein one pair of straps is elastic and the other pair of straps is not elastic; and a pair of curved appendages, each fixed at one end to the waist belt, the appendages further having extensions at the other end, wherein the extensions can connect to each other in front of the vertebrate above the waist belt, and wherein the appendages are capable of attaching to the ends of the straps to connect the straps to the waist belt.

The present invention is additionally directed to methods of supporting the spinal column of a vertebrate. The methods comprise putting one of the above-described devices on the vertebrate such that the device supports the spinal column of the vertebrate. Preferably, the vertebrate is a mammal, most preferably a human.

These methods are particularly useful on a vertebrate that has any of a number of conditions, particularly where adjustment of the amount of spinal movement allowed by the device over the course of treatment is desired. Nonlimiting examples of such conditions are discopathy, discus hernia, antrophy, arthrose, spondilosys, a body deformation, or an injury. Thus, in some preferred embodiments of these methods the device is adjusted on the vertebrate to permit some spinal movement.

Other embodiments within the scope of the claims herein will be apparent to one skilled in the art from consideration of the specification or practice of the invention as disclosed herein. It is intended that the specification be considered exemplary only, with the scope and spirit of the invention being indicated by the following claims.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A dynamic, adjustable orthopedic device for providing support to the spine of a vertebrate, the device comprising:
   (a) a waist belt;
   (b) a vest having portions that are capable of surrounding the torso of the vertebrate above the waist belt, wherein the portions of the vest that surround the torso can attach to each other; and
   (c) a support column comprising:
      (i) an elongated rod attached to the vest and extending substantially the length of the vest adjacent and parallel to the spine of the vertebrate;
      (ii) an elongated spring surrounding the rod and extending substantially the length of the rod, the spring fixed in relation to the rod at the top and bottom of the spring; and
      (iii) a mechanism having a top, a bottom and an adjusting device, the top of the mechanism attached to the vest near a central portion of the rod and the bottom of the mechanism attached to the waist belt, wherein actuating the adjusting device lengthens or shortens the distance from the top to the bottom of the mechanism.

2. The device of claim 1, wherein the mechanism comprises a series of diagonally crossing segments attached at their ends and wherein the adjusting device comprises an adjustment screw and nut for adjusting the degree of separation between the opposing ends of said crossing segments.

3. The device of claim 1, further comprising a horizontal elongated crosspiece attached at its center to the top of the vest near the top of the elongated rod, the ends of the crosspiece capable attaching to the shoulders of the vertebrate.

4. The device of claim 3, wherein the ends of the crosspiece have loops capable of surrounding the arms of the vertebrate at the shoulders.

5. The device of claim 3, wherein the length of the crosspiece is adjustable.

6. The device of claim 1, further comprising at least one pair of straps capable of connecting the vest to the waist belt.

7. The device of claim 6, wherein the at least one pair of straps is elastic.

8. The device of claim 6, wherein the at least one pair of straps is not elastic.

9. The device of claim 6, comprising two pairs of straps, wherein one pair of straps is elastic and the other pair of straps is not elastic.

10. The device of claim 8, further comprising a pair of curved appendages, each fixed at one end to the waist belt, the appendages further having extensions at the other end, wherein the extensions can connect to each other in front of the vertebrate above the waist belt, and wherein the appendages are capable of attaching to the ends of the straps to connect the straps to the waist belt.

11. The device of claim 1, wherein the portions of the vest that surround the torso can attach to each other using hook and loop fasteners.

12. The device of claim 1, wherein the bottom of the spring is fixed to the rod using a mechanism that can raise or lower the bottom or the spring in relation to the rod.

13. The device of claim 1, wherein the device is capable of being adjusted on the vertebrate to permit some spinal movement.

14. The device of claim 1, wherein the vertebrate is a mammal.

15. The device of claim 1, wherein the vertebrate is a human.

16. A dynamic, adjustable orthopedic device for providing support to the spine of a human, the device comprising:
   (a) a waist belt;
   (b) a vest having portions that are capable of surrounding the torso of the vertebrate above the waist belt, wherein the portions of the vest that surround the torso can attach to each other, wherein the portions of the vest that surround the torso can attach to each other using hook and loop fasteners;
   (c) a support column comprising:
      (i) an elongated rod attached to the vest and extending substantially the length of the vest adjacent and parallel to the spine of the vertebrate;
      (ii) an elongated spring surrounding the rod and extending substantially the length of the rod, the spring fixed in relation to the rod at the top and bottom of the spring, wherein the bottom of the spring is fixed to the rod using a mechanism that can raise or lower the bottom or the spring in relation to the rod; and
      (iii) a mechanism having a top, a bottom and an adjusting device, the top of the mechanism attached to the vest near a central portion of the rod and the bottom of the mechanism attached to the waist belt, wherein actuating the adjusting device lengthens or shortens the distance from the top to the bottom of the mechanism, wherein the mechanism comprises a series of diagonally crossing segments attached at their ends and wherein the adjusting device comprises an adjustment screw and nut for adjusting the degree of separation between the opposing ends of said crossing segments;
   (d) a horizontal elongated crosspiece attached at its center to the top of the vest near the top of the elongated rod, wherein the ends of the crosspiece having loops capable of surrounding the arms of the vertebrate at the shoulders, and wherein the length of the crosspiece is adjustable;
   (e) two pairs of straps capable of connecting the vest to the waist belt, wherein one pair of straps is elastic and the other pair of straps is not elastic; and a pair of curved appendages, each fixed at one end to the waist belt, the appendages further having extensions at the other end, wherein the extensions can connect to each other in front of the vertebrate above the waist belt, and wherein the appendages are capable of attaching to the ends of the straps to connect the straps to the waist belt.

17. A method of supporting the spinal column of a vertebrate, the method comprising putting the device of any one of claims 1-16 on the vertebrate such that the device supports the spinal column of the vertebrate.

18. The method of claim 17, wherein the vertebrate is a mammal.

19. The method of claim 17, wherein the vertebrate is a human.

20. The method of claim 17, wherein the vertebrate has discopathy, discus hernia, antrophy, arthrose, spondilosys, a body deformation, or an injury.

21. The method of claim 17, wherein the device is adjusted on the vertebrate to permit some spinal movement.

* * * * *